United States Patent [19]

Dvoretzky

[11] Patent Number: 5,053,024
[45] Date of Patent: Oct. 1, 1991

[54] APPLICATION SYSTEM AND METHOD FOR TREATING WARTS

[76] Inventor: Israel Dvoretzky, 39 Gate Way, Hamden, Conn. 06514

[21] Appl. No.: 425,328

[22] Filed: Oct. 23, 1989

[51] Int. Cl.$^5$ .......................... A61F 7/00; A61M 35/00
[52] U.S. Cl. ..................................... 604/291; 604/290
[58] Field of Search ................ 604/291, 287, 290; 126/204; 128/82.1, 898; 424/447, 443

[56] References Cited

U.S. PATENT DOCUMENTS

| | | | |
|---|---|---|---|
| Re. 32,026 | 11/1985 | Yamashita et al. | 126/204 |
| 2,573,791 | 11/1957 | Howells | 604/291 |
| 4,136,172 | 2/1976 | Walliczek | 424/632 |
| 4,282,005 | 12/1979 | Sato et al. | 126/204 |
| 4,595,591 | 6/1986 | Mardi et al. | 424/718 |
| 4,756,299 | 7/1988 | Podella | 128/399 |
| 4,778,786 | 10/1988 | Reever et al. | 514/164 |
| 4,857,525 | 8/1989 | Philippe et al. | 514/554 |
| 4,868,219 | 9/1989 | Thornfeldt | 514/663 |
| 4,963,360 | 10/1990 | Argaud | 424/447 |

*Primary Examiner*—Randall L. Green
*Assistant Examiner*—R. Clarke
*Attorney, Agent, or Firm*—Melvin I. Stoltz

[57] ABSTRACT

A new application system and method for curing or reducing the pain and discomfort associated with warts is achieved by employing exothermic pads and applying the exothermic pad directly over the wart. In the preferred embodiment, the exothermic pads are constructed to provide long-lasting, continuous heating of the skin surface for at least several hours at a temperature level which will not burn or otherwise injure the skin. In addition, softening agents may be incorporated into the pad to further enhance the efficacy of the exothermic pad.

9 Claims, No Drawings

APPLICATION SYSTEM AND METHOD FOR TREATING WARTS

TECHNICAL FIELD

This invention relates to an application system and method for treating warts and more particularly to a treatment system and method employing the continuous application of heat to the warts.

BACKGROUND ART

Warts are very common and have long presented problems to individuals due to the pain, discomfort and the cosmetic problem associated therewith. Although various methods and treatments have been developed over the years for reducing or eliminating the undesirable effects associated with warts, these prior art applications, treatments and methods have been incapable of eliminating or curing warts or the problems associated with them.

Many different methods have been developed to treat warts. However, none of them are uniformly effective. The most common treatments for eliminating warts are surgery (conventional or laser surgery), cryosurgery, or the application of different acidic chemicals in order to completely remove the affected area. However, for many individuals, these processes are as difficult or as uncomfortable as the wart itself. The warts may return, and patients may be left with scar formation. Consequently, many individuals avoid these treatments and, instead, merely accept the discomfort associated with their warts. Unfortunately, when warts are left alone, they may also spread.

Various chemical compositions have been developed in an attempt to eliminate or reduce the size of the warts by inactivating or slowing the growth of the virus within the skin. In addition, other chemical compounds have been used to reduce or eliminate the overgrowth and keratinization of the wart and thereby lessen its sensitivity or tenderness. Unfortunately, these chemical compositions have been incapable of providing a universally successful treatment for warts and, at best, have only been partially successful.

Therefore, it is a principal object of the present invention to provide an application system and method for treating warts which will completely eliminate the wart by destroying or totally inactivating the wart viruses in virtually most individuals.

Another object of the present invention is to provide an application system and method for treating warts having the characteristic features described above which will be capable of universal application to all different types of cutaneous warts with equal efficacy of results.

Another object of the present invention is to provide an application system and method for treating warts having the characteristic features described above which is capable of being employed by the individual in a convenient, self-administered manner, eliminating the need for repeated medical consultations or painful treatments.

Another object of the present invention is to provide an application system and method for treating warts having the characteristic features described above which can be employed both conveniently and easily, without incurring any discomfort or pain.

Other and more specific objects will in part be obvious and will in part appear hereinafter.

DETAILED DESCRIPTION

The skin is divided into three layers: the epidermis, the dermis, and the subcutaneous tissue. The outer layer of the skin is called the epidermis, and varies in thickness from about 0.3 mm on the eyelids and flexural areas to 1.55 mm on the palms and soles. The outermost layer of the epidermis is the stratum corneum (horny layer), which is comprised of completely keratinized dead cells. The thickness of the stratum corneum varies greatly on different parts of the body, being thickest on the palms and soles and totally absent on the oral mucosa.

The bottommost layer of the epidermis, called the basal cell layer, rests upon the basement membrane separating the epidermis from the dermis. The basal cells are the only epidermal cells that proliferate. The basal cells proliferate and (by cell division) form the keratinocytes (squamous cell layer stratum spinosum, spinous layer). The keratinocytes synthesize insoluble protein which remains in the cells and will eventually become a major component of the outer layer (the stratum corneum horny layer). The keratinocytes continue to divide and to migrate from the bottommost layer to the outermost layer, until the cells finally die. In this process of keratinization, the cells continue to flatten and their cytoplasm appears granular (stratum granulosum, granular layer) until they finally die as they reach the surface to form the stratum corneum (horny layer).

Warts are known to be intra-epidermal tumors of the skin caused by infection with the human papilloma virus (HPV). The HPV induces an abnormal increase of cells in the skin tissue, commonly referred to as hyperplasia, with the hyperplasia being limited to the squamous epithelium. Typically, replication of the papilloma virus is confined to the nuclei of the upper layer of infected epidermal cells.

It has long been known that temperature is an important factor in the development of warts, as well as in treating warts. It is also known that the HPV prefers to produce lesions on cool sites of the body. Since the skin surface in general and the extremities of individuals, such as hands and feet, typically have temperatures of between about 24° and 31° C., (less than the body temperature) these locations are typical for the development of the wart virus. The anogenital warts and laryngeal warts tend to replicate in more warmer locations and are clearly well known as comprising a different HPV.

Various studies have shown that the local application of heat causes the virus organisms to be slowed or inactivated. However, the only attempt to effectively apply heat as a wart treatment was the use of hot water baths, with the individual immersing the entire body part containing the wart into a hot water bath. In view of the inherent limitations of this system as well as its limited success, wide acceptance of hot water exposure was never realized.

In particular, one principal limitation found with hot water baths is the inherent difficulty in maintaining a constant temperature for long time periods. In addition, hot water baths are extremely difficult to employ since the entire body part must be immersed into the hot water and not only the wart. This is particularly difficult since long time exposures are required, as well as repeated exposures several times a day. Furthermore, the hot water bath procedure is particularly hazardous to children, due to the risk of getting severely burned.

Finally, hot water baths are not realistically practical due to the importance of precision in the application temperature. The application temperature is extremely important, since the leeway between a therapeutic temperature and a destructive temperature is very narrow. At 44° C., a six-hour exposure is needed to cause blistering or irreversible damage to the basal layer of the epidermis. However, at 51° C., an exposure of between about 3 to 5 minutes is sufficient to destroy the epidermis.

In the present invention, the difficulties and drawbacks of the prior art systems, methods and procedures have been eliminated and a local, easily employed, convenient consumer-oriented wart treatment system and method is achieved for the first time. In this invention, an exothermic pad is applied directly on the skin surface, thereby providing heat to the precise wart-bearing surface, preventing or impeding the wart's growth. No prior art treatment has ever taught or suggested this concept.

Exothermic pads have been previously developed and typically comprise a porous film or pad of woven or non-woven material incorporating chemicals which will react exothermically in the presence of oxygen. Although any desired chemicals can be employed, exothermic pads typically contain a mixture of alkaline sulfides and iron carbide which are dispersed in two pads. In addition, the pores of the pads are of sufficient size to assure the required air flow is achieved.

Prior to use, the pad is sealed within a pouch using an inert gas, such as nitrogen. As long as the pad remains in the sealed container until use, no chemical reaction takes place. However, once the pad is opened, the presence of the oxygen in the air causes the chemicals to react and the desired exothermic reaction is achieved.

In the present invention, after opening, the pad is applied to the skin at the site of the wart and allowed to remain on the skin for several hours. This procedure may be repeated several times a day. By applying the exothermic pad in this manner, the wart virus is inactivated or slowed in its development, thereby preventing further invasion of the virus to adjacent tissue. As a result, the normal reparative process of the skin takes effect, moving the infected portion to a higher and higher level in the spinous layer of the epidermis, towards the surface of the skin, until the wart is shed in the normal process with the stratum corneum.

By employing the exothermic pad of the present invention, the temperature of the skin is elevated and maintained at about 42°–43° C. for a period of about two hours. Preferably, however, the exothermic pad should remain on the skin for about six to seven hours and then replaced with a new pad. This treatment should continue for several days, as long as the skin surface shows no signs of being adversely affected.

It has been found that the skin can tolerate definite amounts of local hyperthermia without blistering or being damage. Furthermore, it has also been found that the skin surface can tolerate an external temperature of 44° C. without blistering and, even at that temperature, will take at least six hours of continuous exposure before blistering will occur. In addition, even if blistering were to occur, such blistering may well enhance the recovery of warts, since it would eliminate some of the upper layer of the wart. If desired, several layers of sterilized gauze, or similar material, can be placed between the skin surface and the pad to reduce the heat exposure to the skin. One method available to treat warts today is using cryosurgery with liquid nitrogen. In this method, there is blistering formation which is supposed to help in the elimination of the wart.

In the preferred embodiment, the exothermic pad of the present invention also incorporates keratolytic chemical agents which assist in reducing the thickness of the epidermis, particularly the stratum corneum. Inasmuch as the wart viruses are confined to the upper layer of the epidermis, the stratum granulosum and stratum corneum, any removal of the outermost horny layer technically eliminates a portion of the wart as well as the viral particles contained therein, destroying the viral particles by shedding. In addition, the thinning of the stratum corneum enables the heat to penetrate deeper within the wart lesion, thereby achieving greater efficacy from the application of the pad.

Although various keratolytic agents can be incorporated into the exothermic pad in order to reduce the upper layer of the epidermis, it has been found that salicylic acid or salicylic and lactic acid are preferable, since such chemicals may be incorporated into the exothermic pad to attain the desired beneficial results. By incorporating either salicylic acid, salicylic and lactic acid, or other similar chemical compositions, the exothermic pad may operate more effectively, since the thickness of the epidermis is reduced, thereby allowing the heat generated by the exothermic pad to penetrate the wart to a greater extent.

In order to further enhance the efficacy of the present invention, it is preferable to remove the layers of dead skin that have resulted from the application of the keratolytic chemical agents. Consequently, after each exothermic pad of this invention has been employed, it is desirable for the user to gently rub the affected area with an abrasive member, in order to reduce the thickness of the epidermis, particularly the stratum corneum. Typically, any mildly abrasive member may be employed, such as an emery board, manicure nail file, wash cloth, brush, etc. In this way, the process of reducing the thickness of the epidermis is enhanced and the removal of the wart, as well as the inactivation of the wart virus is accomplished more rapidly.

It will thus be seen that the objects set forth above, among those made apparent from the preceding description, are efficiently attained and, since certain changes may be made in carrying out the above method or in employing the system set forth, without departing from the scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what I claim as new and desire to secure by Letters Patent is:

1. A method for treating warts employing an exothermic pad which is constructed from a carrier incorporating a plurality of chemicals selected for reacting exothermically in the presence of oxygen comprising the steps of A. placing the exothermic pad on the surface of the skin bearing the wart; and B. leaving the exothermic pad on the skin surface for an extended time period sufficient to raise the skin surface temperature and maintain the skin surface temperature at the elevated temperature for substantially the entire time period;

whereby the wart virus is inactivated or slowed in its growth by the direct application of heat without any damage to the skin.

2. The method defined in claim 1, wherein said extended time period comprises between about two and seven hours.

3. The method defined in claim 1, comprising the additional steps of

C. removing the pad from the surface of the skin at the end of the time period; and D. repeating steps A through C in order to sequentially apply additional exothermic pads.

4. The method defined in claim 3, wherein the process is continued for several days.

5. The method defined in claim 3, wherein said pad is further defined as incorporating a chemical agent which assists in achieving a local anti-viral or keratolytic effect on the wart.

6. The method defined in claim 5, wherein said keratolytic agent is further defined as comprising one or more selected from the group consisting of salicylic acid and lactic acid.

7. The method defined in claim 5, comprising the additional step of

E. rubbing the skin surface with a mildly abrasive material between applications of the exothermic pad, thereby effectively reducing the thickness of the epidermis and improving the efficacy of the subsequently applied pads.

8. The method defined in claim 7, wherein said mildly abrasive material comprises one selected from the group consisting of emery boards, manicure nail files, brushes and wash cloths.

9. The method defined in claim 1, wherein the temperature of the skin is raised to between about 42°-43° C. for at least two hours.

* * * * *